US007587949B2

(12) United States Patent
Dingmann et al.

(10) Patent No.: US 7,587,949 B2
(45) Date of Patent: Sep. 15, 2009

(54) SYSTEM AND METHOD FOR STIMULATION AND CHARACTERIZATION OF BIOLOGIC MATERIALS

(75) Inventors: David L. Dingmann, St. Paul, MN (US); Frank C. Conati, Minneapolis, MN (US); Troy D. Nickel, Minneapolis, MN (US); Aaron M. Owens, Plymouth, MN (US); Chrysanthi Williams, Minnetonka, MN (US)

(73) Assignee: Bose Corporation, Framingham, MA (US)

( * ) Notice: Subject to any disclaimer, the term of this patent is extended or adjusted under 35 U.S.C. 154(b) by 205 days.

(21) Appl. No.: 11/780,729

(22) Filed: Jul. 20, 2007

(65) Prior Publication Data

US 2009/0019950 A1     Jan. 22, 2009

(51) Int. Cl.
*G01N 1/20* (2006.01)
*G01N 17/00* (2006.01)

(52) U.S. Cl. .................................. 73/863.02; 73/865.6

(58) Field of Classification Search .............. 73/863.02, 73/863.03, 37
See application file for complete search history.

(56) References Cited

U.S. PATENT DOCUMENTS

| | | | |
|---|---|---|---|
| 5,327,774 A | 7/1994 | Nguyen et al. .................. 73/37 |
| 5,379,645 A | 1/1995 | Smart ........................... 73/794 |
| 5,537,335 A | 7/1996 | Antaki et al. ................ 702/100 |
| 5,670,708 A | 9/1997 | Vilendrer ........................ 73/37 |
| 5,739,645 A | 4/1998 | Xia et al. .................... 315/307 |
| 6,416,995 B1 | 7/2002 | Wolfinbarger ............ 435/289.1 |
| 2002/0116054 A1 | 8/2002 | Lundell et al. ............... 623/2.1 |
| 2003/0066338 A1 | 4/2003 | Michalsky et al. ............. 73/37 |
| 2003/0199083 A1* | 10/2003 | Vilendrer et al. ......... 435/297.2 |

FOREIGN PATENT DOCUMENTS

| | | |
|---|---|---|
| GB | 1510163 | 5/1978 |
| JP | 2005337758 | 12/2005 |
| WO | 94/01061 | 1/1994 |
| WO | 00/41648 | 7/2000 |
| WO | 03/078564 | 9/2003 |

OTHER PUBLICATIONS

International Search Report and Written Opinion dated Nov. 20, 2008 for Appl. No. PCT/US2008/070084.
Menzler F. et al, "Dynamic Characterization of a New Accelerated Heart Valve Tester" Asaio Journal, Lippincott Williams & Wilkins/Asaio, Hagertown, MD, US, vol. 43, No. 5, Sep. 1, 1997, pp. 372-377.
Kovacs, S.G., et al., "Prosthetic Valve Selection for a Pulsatile Lvad", Nov. 9, 1989, Images of the Twenty First Century. Seattle, Nov. 9-12, 1989, Proceedings of the Annual International Conference of the Engineering in Medicine and Biology Society, New York, IEEE, US, pp. 162-163.

(Continued)

*Primary Examiner*—Hezron Williams
*Assistant Examiner*—Tamiko D Bellamy

(57) ABSTRACT

A multi-sample biologic material stimulation and characterization system includes individual flow paths for each sample. Each individual flow path can maintain sterile conditions and may be chemically monitored. The mean flow rate and pulsatile flow rate through each sample may be individually controlled. Pressure at the sample is controlled independently of the flow rate through downstream variable flow restrictors. An axial force may be applied to each sample. A radial force may be applied via hydrostatic pressure of chamber fluid surrounding each sample. A real-time controller manages the system and saves information gathered from the transducers and actuators of the system.

5 Claims, 5 Drawing Sheets

OTHER PUBLICATIONS

Mansour, A.A.H., Ed., Yongmin Kim, et al: "In Vitro Assessment of the Flow Characteristics of the Centroal-Axisprosthetic Heart Valve", Images of the Twenty First Century. Seattle, Nov. 9-12, 1989; Proceedings of the Annual International Conference of the Engineering in Medicine and Biology Society, New York, IEEE, US, vol. 11 Part 01/06.

* cited by examiner

SYSTEM AND METHOD FOR STIMULATION AND CHARACTERIZATION OF BIOLOGIC MATERIALS

BACKGROUND

This disclosure relates to systems and methods for stimulating and or monitoring multiple biologic samples under multi-axis stress conditions that simulate expected in-use conditions.

SUMMARY

A multi-sample biologic material stimulation and characterization system includes individual flow paths for each sample. Each individual flow path can maintain sterile conditions and may be chemically monitored. The mean flow rate and pulsatile flow rate through each sample may be individually controlled. Pressure at the sample is controlled independently of the flow rate through downstream variable flow restriction valves. An axial force may be applied to each sample. A radial force may be applied via hydrostatic pressure of chamber fluid surrounding each sample. A real-time controller manages the system and saves information gathered from the transducers and actuators of the system.

One embodiment of the present invention is directed to a system comprising: at least two flow loops, each flow loop having a sample holder, a mean flow pump, and a variable flow restrictor valve, the sample holder holding a sample, the sample characterized by a fluid flow rate and a sample pressure; and a controller operating the mean flow pump and variable flow restrictor valve for each of the at least two flow loops to maintain the fluid flow rate and sample pressure according to a user-defined fluid flow rate and sample pressure for each of the at least two flow loops. In an aspect, the sample holder provides a flow path for the fluid flow rate and transmits an axial stress to the sample. In an aspect, the system further comprises a sample chamber holding the sample holder of the at least two flow loops, the chamber characterized by a chamber pressure controlled by the controller. In an aspect, the sample holder further comprises a membrane, the membrane attached over a sample grip and covering a portion of the sample, the membrane maintaining separation of the sample characterized by the sample pressure and the sample chamber characterized by the chamber pressure. In an aspect, the chamber pressure is adjusted by the controller according to a user-defined radial stress profile, the radial stress profile based on a difference between the chamber pressure and the sample pressure. In an aspect, each of the at least two flow loops further includes a pulsatile flow pump, the pulsatile flow pump generating a pulsatile flow rate of fluids to the sample. In an aspect, at least one of the at least two flow loops includes at least one chemical sensor measuring a characteristic of the fluid flow. In a further aspect, the at least one chemical sensor is selected from a group comprising a pH sensor, a dissolved oxygen sensor, a carbon dioxide sensor, an electrical conductivity sensor, a lactate/glucose concentration sensor, a temperature sensor, and a pressure sensor. In an aspect, the at least two flow loops maintain a sterile fluid flow through each sample in the at least two flow loops. In a further aspect, at least one of the at least two flow loops are closed. In an aspect, at least two of the at least two flow loops share a common fluid reservoir. In a further aspect, the common fluid reservoir is maintained at atmospheric pressure. In an aspect, the system further comprises at least one chemical sensor measuring a characteristic of the flow from the common fluid reservoir. In a further aspect, the at least one chemical sensor is selected from a group comprising a pH sensor, a dissolved oxygen sensor, a carbon dioxide sensor, an electrical conductivity sensor, a lactate/glucose concentration sensor, a temperature sensor, and a pressure sensor. In an aspect, at least one of the at least two flow loops includes an upstream pressure transducer measuring a pressure of the fluid flow upstream of the sample and a downstream pressure transducer measuring a pressure of the flow downstream of the sample. In a further aspect, the sample pressure is estimated by an average of the upstream pressure and the downstream pressure. In a further aspect, the fluid flow rate is estimated by a difference of the upstream pressure and downstream pressure. In an aspect, at least one of the at least two flow loops are open. In an aspect, the variable flow restriction valve includes a cam mounted on a shaft of a stepper motor operated by the controller, the cam acting on a flow tube in fluid communication with the sample flow loop to cause a restriction of the flow tube, the amount of restriction depending on a rotational position of the shaft. In an aspect, the sample is a tubular structure.

Another embodiment of the present invention is directed to a system comprising: a chamber flow loop including a sample chamber, the sample chamber characterized by a chamber pressure, the chamber pressure determined by a chamber pump upstream of the sample chamber and a chamber flow restriction valve downstream of the sample chamber; a sample flow loop including a sample holder disposed in the sample chamber, a mean flow pump, a pulsatile flow pump, and a variable flow restriction valve; and a controller operating the mean flow pump and the pulsatile flow pump to provide a user-defined pulsatile fluid flow rate to a sample in the sample holder, the controller operating the variable flow restriction valve to maintain a sample pressure according to a user-defined sample pressure, the controller operating the chamber flow restriction valve to cause a pressure difference between the sample pressure and the chamber pressure, the pressure difference proportional to a user-defined radial stress applied to the sample. In an aspect, the system further comprises a plurality of sample holders disposed in the sample chamber, each of the plurality of sample holders holding a sample and having an associated flow loop, each of the associated flow loops having a mean flow pump, a pulsatile flow pump, and a variable flow restriction valve operated by the controller. In an aspect, the sample is held between a first porous platen and a second porous platen, the first and second porous platens applying an axial stress to the sample. In an aspect, the variable flow restriction valve includes a cam mounted on a shaft of a stepper motor operated by the controller, the cam acting on a flow tube in fluid communication with the sample flow loop to cause a restriction of the flow tube, the amount of restriction depending on a rotational position of the shaft. In an aspect, the sample is a tubular structure.

Another embodiment of the present invention is directed to a method comprising: providing a flow loop having a sample holder supporting a sample, the sample holder disposed in a sample chamber characterized by a chamber pressure; operating a mean flow pump in fluid communication with the flow loop, the mean flow pump providing a fluid medium to the sample at a user-defined fluid flow rate; operating a variable flow restriction valve in fluid communication with the flow loop and disposed downstream of the sample holder, the variable flow restriction valve controlling a sample pressure according to a user-defined sample pressure; and operating a chamber flow restriction valve in fluid communication with the sample chamber and disposed downstream of the sample chamber, the chamber flow restriction valve controlling the chamber pressure to create a difference between the sample pressure and the chamber pressure that is proportional to a user-defined radial stress applied to the sample. In an aspect, the method further comprises applying an axial load to a platen in contact with the sample, the axial load proportional to a user-defined axial stress. In an aspect, the method further comprises providing a plurality of flow loops, each of the plurality of flow loops having a sample holder supporting a sample, each sample characterized by a sample pressure, a mean flow pump, and a variable flow restriction valve, each of the sample holders disposed in the sample chamber; and operating at least one of the variable flow restriction valves according to a first user-defined sample pressure. In an aspect, the first user-defined sample pressure is the same for each sample in the plurality of flow loops. In an aspect, the method further comprises operating at least one of the variable flow restriction valves according to a second user-defined sample pressure.

BRIEF DESCRIPTION OF THE DRAWINGS

In the accompanying drawings, like reference numerals refer to like structural elements and features. Unless otherwise noted, the drawings are not to scale.

FIG. 4b is a front view of the variable flow restriction valve of FIG. 4a.

DETAILED DESCRIPTION

Figure 1:
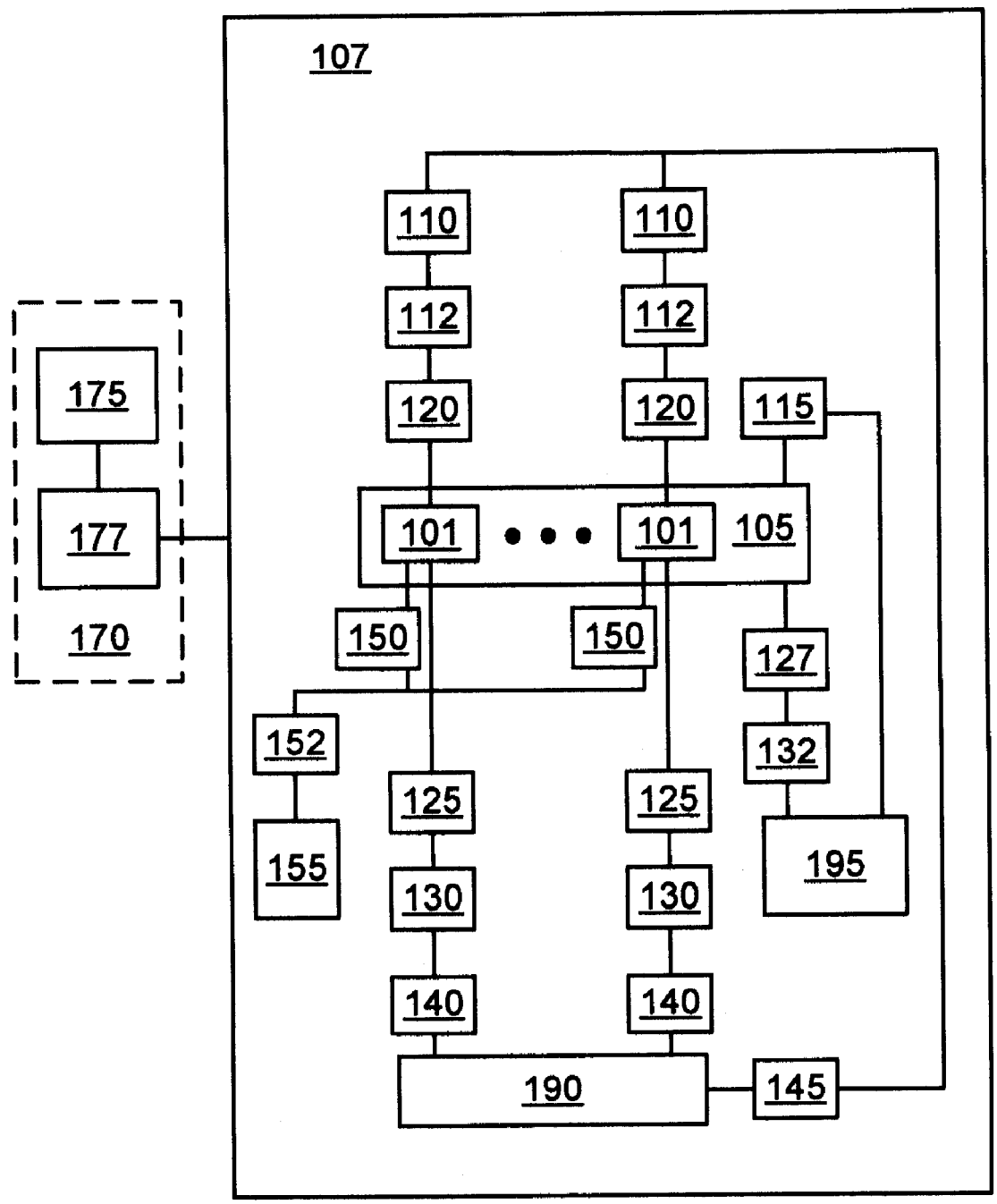
FIG. 1 is block diagram of an embodiment of the present invention.

FIG. 1 is a block diagram of an example of a multi-sample stimulation and characterization system for biologic materials. In FIG. 1, sample holder 101 is enclosed in a sample chamber 105. Each sample holder 101 holds a sample. The sample may be a biologic material, a synthetic material, or a combination of a biologic material and a synthetic material. Examples of a biologic material include native tissue, processed tissue, cell-seeded biomaterial scaffolds, and tissue-engineered constructs. Examples of a synthetic material include medical devices and acellular biomaterials and scaffolds. The sample holders 101 may hold the same type of biologic material or may hold different types of biologic materials.

Each sample is supported with a separate flow loop that maintains sterile conditions within the individual flow loops. For clarity, FIG. 1 shows two flow loops but other embodiments may support more than two flow loops. Each flow loop includes a mean flow pump 110, a pulsatile flow pump 112, an upstream pressure transducer 120, a sample holder 101, a downstream pressure transducer 125, a variable flow restriction valve 130, and one or more chemical process sensors 140. In another embodiment, the one or more chemical process sensors 140 may monitor a combined flow from two or more of the individual flow loops.

Each flow loop transports a fluid medium to and from the sample. The fluid medium may be selected by the user based on the sample. Examples of the fluid medium include distilled water, saline solution, blood or blood substitutes, and cell culture medium.

In the example shown in FIG. 1, each individual flow loop discharges into a common reservoir 190 where components of the fluid medium in the flow loops may be adjusted according to the one or more chemical process sensors 140. In another embodiment, an individual flow loop may be an open flow loop that discharges into a waste reservoir and is not recycled through the flow loop. In another embodiment, an individual flow loop may be discharged into an individual reservoir that is kept separate from the other flow loops thereby accommodating different fluid mediums and/or different sample types in a same run. Although reservoir 190 maintains sterile conditions within each flow loop, the reservoir may be maintained at atmospheric pressure.

A second set of chemical process sensors 145 monitors one or more of the components of the fluid medium delivered to each individual sample from reservoir 190. In embodiments where each flow loop is supplied from a separate reservoir, each flow loop may have a set of chemical process sensors to monitor the fluid medium delivered to each sample. In such embodiments, the user may vary the fluid medium composition supplied to each sample and find an optimum fluid medium composition for the biologic sample.

Chemical process sensors 140, 145 may include, for example, temperature sensors, pH sensors, electrical conductivity sensors, carbon dioxide sensors, dissolved oxygen sensors, and lactate/glucose concentration sensors. In addition to providing environmental information such as temperature and pH, chemical process sensors 140, 145 can provide metabolic information of a live sample by measuring and comparing the pH, dissolved oxygen and lactate/glucose concentration upstream and downstream of the sample.

Mass flow rate of the fluid medium through each flow loop is controlled by the flow loop's mean flow pump 110 and pulsatile flow pump 112. Although FIG. 1 illustrates an embodiment having a separate mean flow pump and pulsatile flow pump, a single mass flow pump providing a pulsatile flow having a mean flow component and an oscillating flow component may be used. Mean flow pump 110 provides a steady mean flow through the flow loop while maintaining sterile conditions of the flow loop. An example of a mean flow pump is a gear pump. The gear pump preferably comprises pump components that can be easily disassembled, sterilized, and reassembled between each use. Each gear pump may be calibrated during production such that the flow rate of the pump as a function of input voltage and pressure is determined and saved for use by a controller 170.

Pulsatile flow pump 112 provides a pulsatile flow on top of the mean flow rate through the flow loop and may be a bellows-type pump such as those described in U.S. Pat. No. 5,670,708, filed on Apr. 2, 1996 and incorporated herein in its entirety. Examples of other pump types that may be used as a pulsatile flow pump include syringe pumps, diaphragm pumps, and piston pumps. The inventors believe that pulsatile flow more closely simulates an in-use condition for some types of samples and creates a stress state that encourages a sample to develop similarly to in-vivo development of the same sample type. Pulsatile flow represents one stimulation axis of a multi-axis stimulation and characterization system. Other stimulation axes may include, for example, bending stress, torsion, axial stress, and radial stress.

An upstream pressure transducer 120 measures the pressure of the fluid medium upstream of the sample. A downstream pressure transducer 125 measures the pressure of the fluid medium downstream of the sample. In some embodiments, the pressure at the sample is estimated by the average of the upstream pressure transducer 120 and the downstream pressure transducer 125. Other embodiments may use a weighted average of the upstream and downstream pressure transducers or may use more complicated functions to estimate the sample pressure that are based on simulations and/or measurements of a specific system design.

A variable flow restriction valve 130 is used to control the sample pressure independently of the mass flow rate. In typical bioreactor designs where a pump determines the mass flow rate through the sample, the pressure at the sample is a determined by the mass flow rate and cannot be set to an arbitrary value without changing the mass flow rate. By incorporating a variable flow restriction valve downstream of the sample, the pressure at the sample may be controlled independently of the mass flow rate through the sample in the sense that a user may specify an arbitrary combination of mass flow rate and pressure values and adjust the variable flow restriction valve and mean flow pump to maintain that combination of mass flow rate and pressure values.

In the example shown in FIG. 1, the mass flow rate may be estimated by a pressure drop between the upstream pressure transducer 120 and the downstream pressure transducer 125 while the pressure at the sample may be controlled by the variable flow restriction valve 130. For example, at the same mass flow rate, indicated by the same pressure drop between the upstream and downstream pressure transducers, the sample pressure may be lowered by opening up the flow restriction valve such that the pressure drop across the variable flow restriction valve 130 is decreased. Conversely, the sample pressure may be increased by restricting the flow restriction valve such that the pressure drop across the variable flow restriction valve 130 increases.

Sample chamber 105 and the fluid flow lines are preferably housed within an environmental chamber 107 such as an incubator. The environmental chamber 107 provides a controlled temperature and atmospheric environment for the samples. For example, cells in a biologic sample may die if the temperature drops below 36° C. and fluid medium components may begin to degrade or denature and lose their activity if the temperature rises above 38° C. In a preferred embodiment, the temperature of the environmental chamber 107 may be set to a user-specified temperature and maintained to within ±0.2° C. of the user-specified temperature by the chamber's controller or by controller 170.

The sample chamber 105 is filled with a chamber fluid that is part of a chamber flow loop that controls a pressure in the sample chamber 105. The chamber flow loop includes a chamber fluid reservoir 195, a chamber pump 115, a pressure transducer 127, and a chamber flow restriction valve 132. The sample chamber 105 is fed by a chamber fluid reservoir 195 through chamber pump 115. A pressure transducer 127 measures the pressure within the sample chamber 105 and a chamber flow restriction valve 132 located downstream of the sample chamber 105 controls the pressure within the sample chamber 105 independently of the chamber flow through the sample chamber 105. In some embodiments, the chamber pump may provide both a mean flow rate and a pulsatile flow rate to generate a pulsatile pressure in the sample chamber. The chamber fluid may be a hydraulic fluid, distilled water, saline solution, blood or blood substitutes, or cell culture medium. Selection of the chamber fluid may be made based on a variety of factors such as, for example, sample type and sample configuration. In some embodiments where a barrier is maintained between the sample and the sample chamber, a simpler pneumatic system may provide the pulsatile pressurization of the sample chamber and replace the chamber flow loop.

A radial stress may be applied to each sample by controlling a pressure of the sample chamber 105. The difference between the chamber pressure and the sample pressure in each flow loop generates a radial stress applied to the sample that is proportional to the difference between the chamber pressure and the sample pressure in the associated flow loop. Since the sample pressure in each flow loop may be individually adjusted, the user can operate the system to apply a different radial stress to each sample, the same radial stress to each sample, or a combination where a first subset of the samples are subjected to a first radial stress state and a second subset of the samples are subjected to a second radial stress state.

An axial compressive stress may be applied to each sample 101. A load cell 150 measures a compressive force applied to the sample and a linear displacement transducer such as an LVDT measures a displacement of a push rod driven by a motor 155 such as a linear motor.

Each motor, actuator, transducer, and sensor is controlled by a controller 170. The controller 170 includes a computer 175 executing a computer program that manages the system. Although FIG. 1 indicates a single computer, it should be understood that more than one computer or a computer having more than one processor may be used to manage different aspects of the system and may be networked with each other and to other computers on the network. Interface electronics 177 provide signal conditioning and communication between the motors, actuators, and transducers of the system and the executing computer program.

In some embodiments, controller 170 may be a software/hardware testing platform for machines such as the WinTest® PCI-Control platform available from the ElectroForce Systems Group of Bose Corporation of Eden Prairie, Minn. The platform preferably includes a user interface module, control/interface electronics, a control software module, a data acquisition module, and a data analysis module. The user interface module is configured to prompt and receive from the user, configuration and parameter data for managing an experimental run and to display current status of an ongoing experimental run or results of a completed or partially completed experimental run. The user interface module may include a reporting module configured to record and save data generated during an experimental run and alert/alarm modules for notifying and/or rectifying out-of-process conditions. Control/interface electronics include circuitry that provides communication/translation between the motors, actuators, and transducers of the system and the executing computer program. The control software module controls the motors and actuators based, in part, on the state of the motors and actuators and data received from the transducers according to user defined parameters characterizing the experimental run conditions. The data acquisition module may be configured to provide low level signal conditioning and translation/conversion of the signals received from transducers that characterize a state of a motor or actuator or characterize an experimental condition such as, for example, pressure, temperature, dissolved oxygen, etc. The data analysis module may be configured to provide statistical analysis of a multi-sample experimental run and provide graphical data display to the user.

Configuration data may include information such as sample holder size and transducer placement and properties. In some embodiments, transducer placement information and property information such as, for example, output voltage or current per pressure or temperature may be entered by the manufacturer and stored by the control platform thereby relieving the user from entering such information. Parameter data may include information about an experimental run and includes a run/growth duration and desired profiles for each stimulation axes such as, for example, pulsatile flow profile, axial stress profile, and radial stress profile. Each profile may be characterized by a peak-to-peak value and a frequency. Alternatively, instead of providing a peak-to-peak value, a cycle shape may be entered by the user. The user may enter more than one profile for each stimulation axis and designate one or more conditions that determine when the associated profile is selected.

Figure 2:
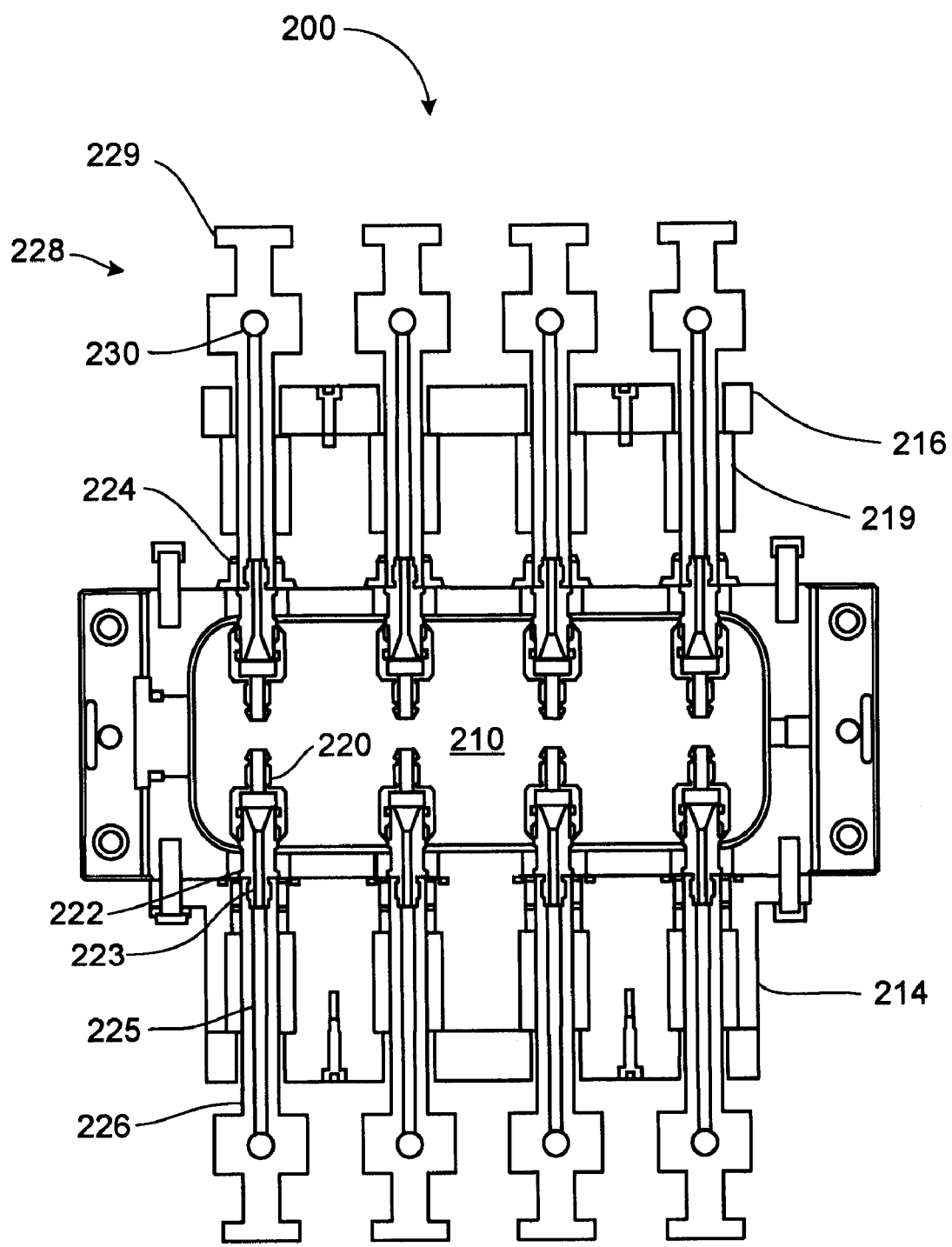
FIG. 2 is a sectional view of an illustrative example of a chamber assembly.

FIG. 2 is a sectional view of an illustrative example of a chamber assembly 200. Chamber assembly 200 includes a sample chamber 210 and one or more sample holders. In the example shown in FIG. 2, sample chamber 210 accommodates four sample holders. Each sample holder includes an upper and lower assembly that holds the sample, provide the fluid flow to the sample, and apply an axial stress to the sample. Each upper and lower assembly includes a sample grip 220, a chamber port assembly 222, and an extension arm 226. Each upper assembly is slidably supported by a bushing or bearing 219 attached to an upper support 216. Each lower assembly is supported by bushing 219 attached to a lower support 214.

Each sample grip 220 includes a barbed end over which a sample membrane is attached. The sample membrane maintains a sterile barrier between the sample and the surrounding chamber fluid in the sample chamber. The sample grip 220 has an interior lumen shaped to accommodate a porous platen that delivers the fluid medium to the sample and also transmits an axial force to the sample. The chamber port assembly 222 includes a first end that is attached to the sample grip 220 and a second end attached to the extension arm 226. A rolling diaphragm 224 allows vertical displacements relative to the chamber wall while maintaining a seal between the chamber interior and exterior. The chamber port assembly 222 has a lumen 223 that is part of the flow loop of the sample. Similarly, extension arm 226 includes an interior lumen 225 that mates with the interior lumen 223 of the chamber port assembly 222 and forms part of the flow loop of the sample. A flow port 230 located near the exterior end 228 of the extension arm 226 is in fluid communication with the interior lumens 223, 225 and provides a connection point to an exterior remainder of the flow loop of the sample.

Exterior end 228 includes an end flange 229 that permits easy mounting/dismounting of the chamber assembly 200 from the system. The end flange 229 is sized to fit into an external grip (not shown) attached to the system. In the example shown in FIG. 2, the upper external grip is attached to a load cell that measures the axial load applied to the sample and the lower external grip is linked to a motor that applies the axial load to the sample.

Figure 3A:
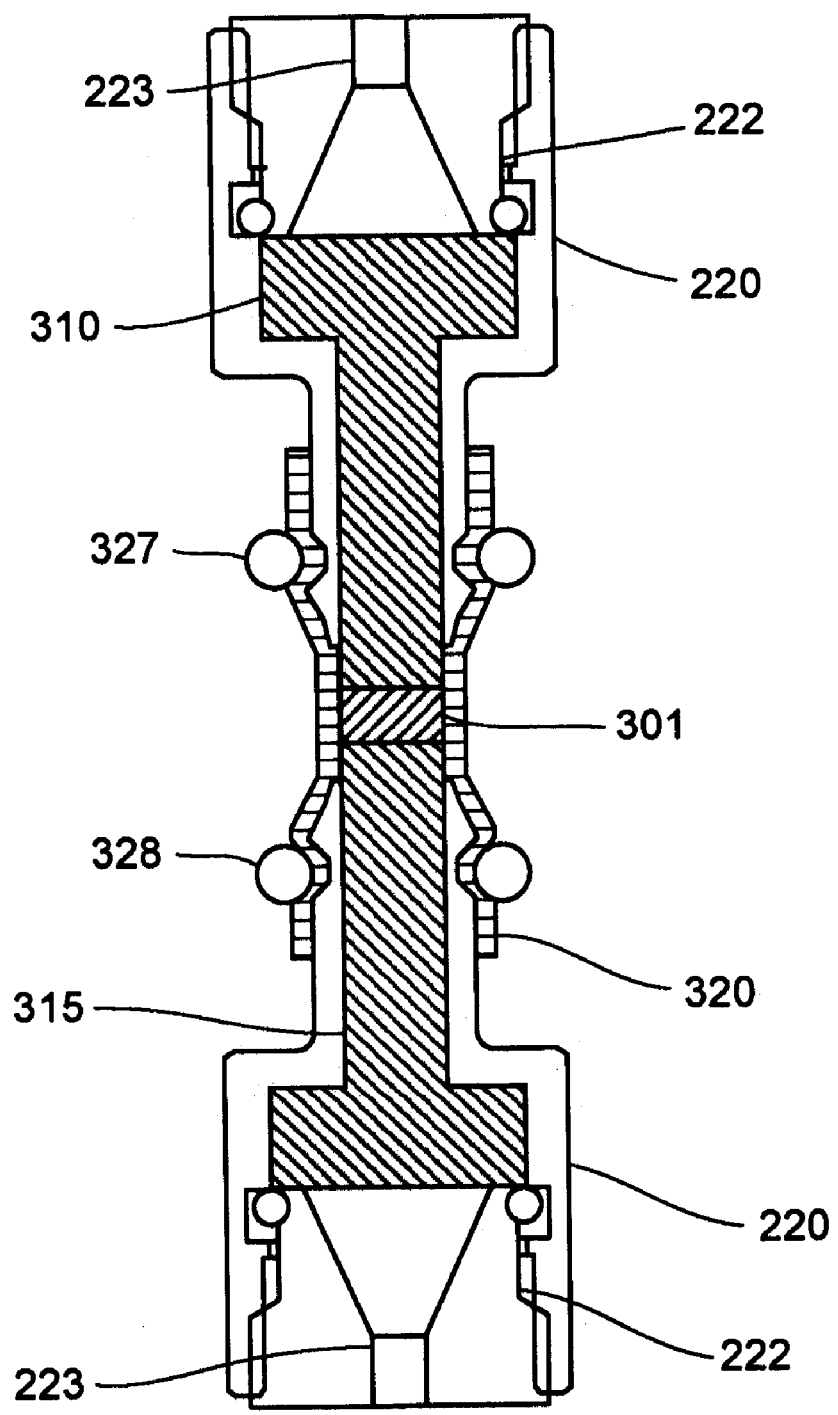
FIG. 3a is a sectional view of the sample grip shown in FIG. 2.

FIG. 3a is a sectional view of the sample grip shown in FIG. 2. In FIG. 3a, sample 301 is held between an upper porous platen 310 and a lower porous platen 315. The sample 301 may be a single sample or a plurality of samples in a stacked configuration. Each porous platen 310, 315 is supported by sample grip 220 and chamber port assembly 222. Fluid medium is supplied to the sample 301 via the lumen 223 of the chamber port assembly 222 and through a porous structure of the porous platen 310, 315. Each porous platen 310, 315 preferably comprises stainless steel although other biologically inert materials such as titanium, zirconia, or bioinert polymers such as polystyrene or polypropylene may be used. Each porous platen 310, 315 may be characterized as a bi-continuous composite having a continuous pore structure and a continuous solid phase such as stainless steel. The continuous pore structure enables fluid medium to flow through the porous platen 310, 315 to the sample 301. The porous platen 310, 315 may be characterized by an average pore size. The average pore size may be selected by the user and may depend on factors such as sample type and available pump head. The average pore size is preferably in the range of 10 μm to 200 μm and more preferably in the range of 40 μm to 100 μm.

The ends of a membrane 320 are fitted over a barbed portion of the upper and lower grips 220 and held in place by an upper O-ring 327 and a lower O-ring 328. The membrane 320 covers a portion of the upper porous platen 310, a portion of the lower porous platen 315, and a portion of the sample 301. The upper and lower O-rings 327, 328 seal the membrane 320 against grips 220 such that the membrane 320 maintains a sterile condition within the sample 301 and acts as a barrier preventing contamination of the sample 301 by the chamber fluid filling the sample chamber 210.

Membrane 320 preferably is a flexible, biocompatible material. Membrane 320 preferably is transparent to allow viewing of the sample 301 during a run. In some embodiments, membrane 320 comprises a silicone membrane between 75 μm and 350 μm thick and more preferably between 100 μm and 150 μm thick.

Figure 3B:
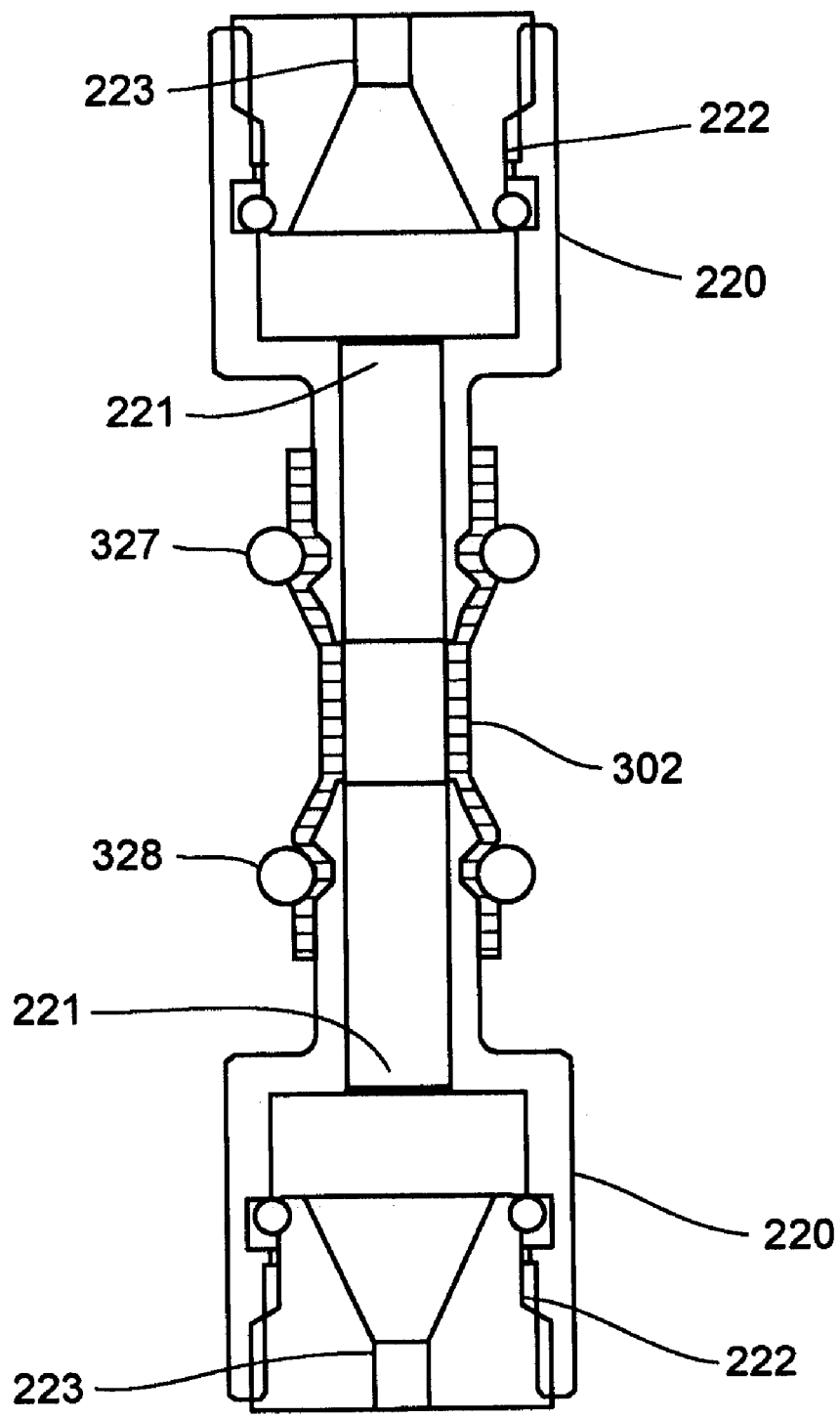
FIG. 3b is a sectional view of the sample grip shown in FIG. 2 with a different sample type.

FIG. 3b is a sectional view of the sample grip shown in FIG. 2 with a different sample type. In FIG. 3b, sample 302 is a tubular structure instead of a disk-shaped structure shown in FIG. 3a. The tubular structure may be a blood vessel such as, for example, an artery or vein, a trachea or a bladder. In FIG. 3b, the interior lumen 221 of the sample grip 220 provides a flow path for the fluid medium to the sample 302. The ends of the tubular sample are fitted over the barbed portion of the upper and lower grips 220 and held in place by an upper O-ring 327 and a lower O-ring 328. An axial tensile or compressive stress may be generated in the sample 302 by displacing the grips vertically relative to each other. A radial stress may be applied to the sample 302 by creating a pressure difference between the pressure in the sample holder and the pressure in the sample chamber. In the configuration shown in FIG. 3b, the sample acts as the membrane in FIG. 3a and is in direct contact with the chamber fluid. In another configuration, a membrane may be fitted over the sample 302 and held in place by the upper O-ring 327 and the lower O-ring 328 to maintain a barrier between the chamber fluid and the sample 302.

Figure 4A:
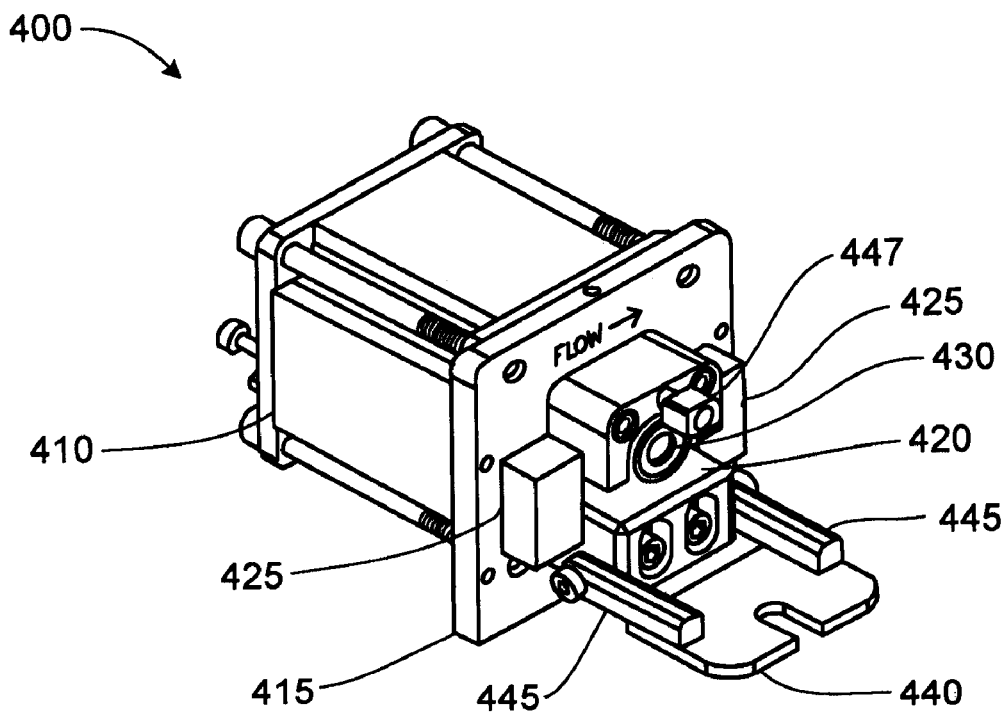
FIG. 4a is a perspective view of an example of a variable flow restriction valve.
Figure 4B:
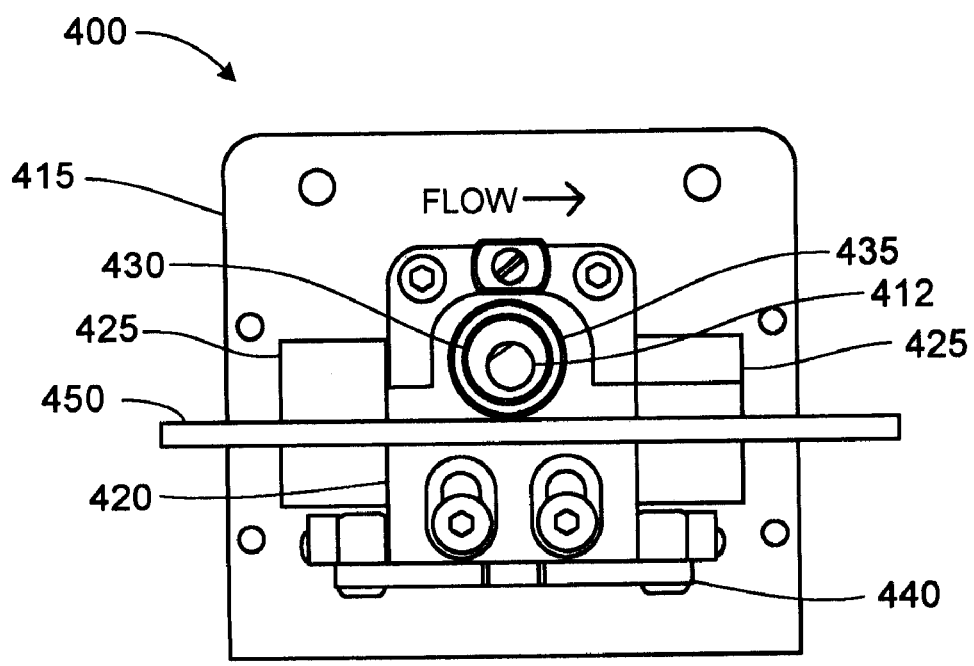

FIG. 4a is a perspective view of an example of a variable flow restriction valve and FIG. 4b is a front view of the variable flow restriction valve shown in FIG. 4a. A stepper motor 410 is attached to a motor mount plate 415. The stepper motor may be a brushless motor such as, for example, those available from Applied Motion Products Inc. of Watsonville, Calif. In other embodiments, a rotary servomotor or a linear servomotor may be used instead of a stepper motor. A drive shaft 412 of the stepper motor 410 extends through an opening in the motor mount plate 415. A cam 430 is attached to the drive shaft 412. A sleeve bushing 435 may be mounted on the cam 430 to reduce a shear stress generated by the rotation of the cam 430 on a flow tube 450. The sleeve bushing 435 preferably comprises a low friction material such as, for example, polyoxymethylene, ultra high-molecular weight polyethylene, or polytetrafluoroethylene. The cam 430 may have a circular cross-section that is mounted to the drive shaft 412 such that a cam axis is parallel to but displaced from the drive shaft axis.

The flow tube 450 is placed between a vertically adjustable block 420 and the cam 430. The flow tube 450 transports fluid medium between the sample holder 101 and the downstream chemical process sensors 140 and provides a barrier preventing contamination of the fluid medium from contamination sources external to the flow loop. The block 420 is adjusted vertically to accommodate flow tubes of varying diameters and is adjusted such that the rotation of the cam encompasses a fully opened flow tube state and a substantially closed flow tube state. The flow tube 450 is restrained in a direction parallel to the drive shaft axis by a pair of foam cushions 425 and a pair of pivoting hinges 445. The pivoting hinges 445 are attached to a door 440 that pivots downward to allow easy mounting and dismounting of the flow tube 450 to or from the valve 400. After the flow tube 450 is mounted in the valve 400, the door 440 is pivoted vertically and latched in the vertical position by door latch 447. When the door is latched in the vertical position, the pair of pivoting hinges 445 presses the flow tube 450 against the foam cushions 425 and holds the flow tube 450 in place without restricting the flow in the flow tube.

During operation, rotation of the cam causes the flow tube 450 to be restricted or opened depending on the direction of cam rotation. For example, in the configuration shown in FIG. 4b, when the drive shaft 412 is rotated counter-clockwise, the rotation of the cam 430 presses the sleeve bushing 435 against the flow tube 450 causing a restriction in the flow tube 450. The magnitude of restriction caused by the cam 430 depends on a rotational position of the cam. In the example shown in FIG. 4b, the restriction of the flow tube increases as the cam is rotated counter-clockwise and the restriction of the flow tube decreases as the cam is rotated clockwise.

When the cam 430 is rotated such that the cross-sectional area of the flow tube is restricted or reduced, the pressure drop across the valve 400 increases for a given mass flow rate through the flow tube 450. The increased pressure drop across the valve 400 increases the pressure at the sample. Conversely, when the cam 430 is rotated such that the cross-sectional area of the flow tube is increased or opened, the pressure drop across the valve 400 decreases for a given mass flow rate through the flow tube 450. The decreased pressure drop across the valve 400 decreases the pressure at the sample. By controlling the flow tube restriction, the pressure drop across the valve 400 and the pressure at the sample can be controlled independently of the mass flow rate through the sample.

Embodiments of the systems and methods described above comprise computer components and computer-implemented steps that will be apparent to those skilled in the art. For example, it should be understood by one of skill in the art that the computer-implemented steps may be stored as computer-executable instructions on a computer-readable medium such as, for example, floppy disks, hard disks, optical disks, Flash drives, Flash ROMS, nonvolatile ROM, and RAM. Furthermore, it should be understood by one of skill in the art that the computer-executable instructions may be executed on a variety of processors such as, for example, microprocessors, digital signal processors, gate arrays, etc. For ease of exposition, not every step or element of the systems and methods described above is described herein as part of a computer system, but those skilled in the art will recognize that each step or element may have a corresponding computer system or software component. Such computer system and/or software components are therefore enabled by describing their corresponding steps or elements (that is, their functionality), and are within the scope of the present invention.

Having thus described at least illustrative embodiments, various modifications and improvements will readily occur to those skilled in the art and are intended to be within the scope of the invention. Accordingly, the foregoing description is by way of example only and is not intended as limiting. The invention is limited only as defined in the following claims and the equivalents thereto.

What is claimed is:

1. A system comprising:
a chamber flow loop including a sample chamber, the sample chamber characterized by a chamber pressure, the chamber pressure determined by a chamber pump upstream of the sample chamber and a chamber flow restriction valve downstream of the sample chamber;
a sample flow loop including a sample holder disposed in the sample chamber, a mean flow pump, a pulsatile flow pump, and a variable flow restriction valve; and
a controller operating the mean flow pump and the pulsatile flow pump to provide a user-defined pulsatile fluid flow rate to a sample in the sample holder, the controller operating the variable flow restriction valve to maintain a sample pressure according to a user-defined sample pressure, the controller operating the chamber flow restriction valve to cause a pressure difference between the sample pressure and the chamber pressure, the pressure difference proportional to a user-defined radial stress applied to the sample.

2. The system of claim 1 further comprising a plurality of sample holders disposed in the sample chamber, each of the plurality of sample holders holding a sample and having an associated flow loop, each of the associated flow loops having a mean flow pump, a pulsatile flow pump, and a variable flow restriction valve operated by the controller.

3. The system of claim 1 wherein the sample is held between a first porous platen and a second porous platen, the first and second porous platens applying an axial stress to the sample.

4. The system of claim 1 wherein the variable flow restriction valve includes a cam mounted on a shaft of a stepper motor operated by the controller, the cam acting on a flow tube in fluid communication with the sample flow loop to cause a restriction of the flow tube, the amount of restriction depending on a rotational position of the shaft.

5. The system of claim 1 wherein the sample is a tubular structure.

* * * * *